US010646635B2

(12) United States Patent
Pohlmeier et al.

(10) Patent No.: US 10,646,635 B2
(45) Date of Patent: May 12, 2020

(54) METHOD AND APPARATUSES FOR PREPARING AN EXTRACORPOREAL BLOOD CIRCUIT FOR THE TREATMENT OF BLOOD

(71) Applicant: Fresenius Medical Care Deutschland GmbH, Bad Homburg (DE)

(72) Inventors: Robert Pohlmeier, Bad Homburg (DE); Wofgang Wehmeyer, Tübingen (DE)

(73) Assignee: Fresenius Medical Care Deutschland GmbH, Bad Homburg (DE)

( * ) Notice: Subject to any disclaimer, the term of this patent is extended or adjusted under 35 U.S.C. 154(b) by 448 days.

(21) Appl. No.: 15/513,187

(22) PCT Filed: Sep. 22, 2015

(86) PCT No.: PCT/EP2015/071677
§ 371 (c)(1),
(2) Date: Mar. 22, 2017

(87) PCT Pub. No.: WO2016/046177
PCT Pub. Date: Mar. 31, 2016

(65) Prior Publication Data
US 2017/0304522 A1    Oct. 26, 2017

(30) Foreign Application Priority Data
Sep. 23, 2014   (DE) .................. 10 2014 113 728

(51) Int. Cl.
*A61M 1/36* (2006.01)
*A61K 31/194* (2006.01)

(52) U.S. Cl.
CPC ......... *A61M 1/3649* (2014.02); *A61K 31/194* (2013.01); *A61M 1/3643* (2013.01);
(Continued)

(58) Field of Classification Search
CPC .............. A61M 1/3649; A61M 1/3644; A61M 1/3643; A61M 1/3672; A61K 31/194
See application file for complete search history.

(56) References Cited

U.S. PATENT DOCUMENTS

| 4,850,998 A | 7/1989 | Schoendorfer |
| 5,004,548 A | 4/1991 | Richalley et al. |

(Continued)

FOREIGN PATENT DOCUMENTS

| CA | 2863 264 | 9/2007 |
| CA | 2643140 | 9/2007 |

(Continued)

OTHER PUBLICATIONS

International Search Report for International Application No. PCT/EP2015/071677, dated Nov. 12, 2015, 6 pages (with English translation).

(Continued)

*Primary Examiner* — Ariana Zimbouski
(74) *Attorney, Agent, or Firm* — Fish & Richardson P.C.

(57) ABSTRACT

The present disclosure concerns a method for preparing an extracorporeal blood circuit for its use in a blood treatment of a patient, which treatment is carried out using a blood treatment apparatus and using a blood treatment device, which comprises a blood chamber and a dialysate chamber partitioned off therefrom by a membrane, The method comprising: filling the extracorporeal blood circuit using a priming solution, wherein the priming solution comprises citrate, or filling of the extracorporeal blood circuit using a priming solution and using a citrate solution. The invention further comprises devices suitable for carrying out the method.

16 Claims, 1 Drawing Sheet

(52) U.S. Cl.
CPC ........ *A61M 1/3644* (2014.02); *A61M 1/3672* (2013.01); *A61M 2202/0445* (2013.01); *A61M 2205/12* (2013.01); *A61M 2205/50* (2013.01)

(56) References Cited

U.S. PATENT DOCUMENTS

| | | | |
|---|---|---|---|
| 5,776,345 A | 7/1998 | Truitt et al. | |
| 6,830,553 B1 * | 12/2004 | Burbank ................. | A61M 1/34 210/321.6 |
| 2006/0037910 A1 | 2/2006 | Shah et al. | |
| 2009/0221948 A1 * | 9/2009 | Szamosfalvi ....... | A61M 1/3672 604/6.07 |
| 2011/0237996 A1 | 9/2011 | Kotanko et al. | |
| 2012/0203159 A1 * | 8/2012 | Pohlmeier ........... | A61M 1/3675 604/6.07 |

FOREIGN PATENT DOCUMENTS

| | | |
|---|---|---|
| DE | 69428220 | 6/2002 |
| DE | 102009018664 | 10/2010 |
| DE | 102009024468 | 12/2010 |
| WO | WO9219153 | 11/1992 |
| WO | WO0137900 | 5/2001 |
| WO | WO 2007/101064 | 9/2007 |

OTHER PUBLICATIONS

International Preliminary Report on Patentability in Application No. PCT/EP2015/071677, dated Mar. 28, 2017, 6 pages.

* cited by examiner

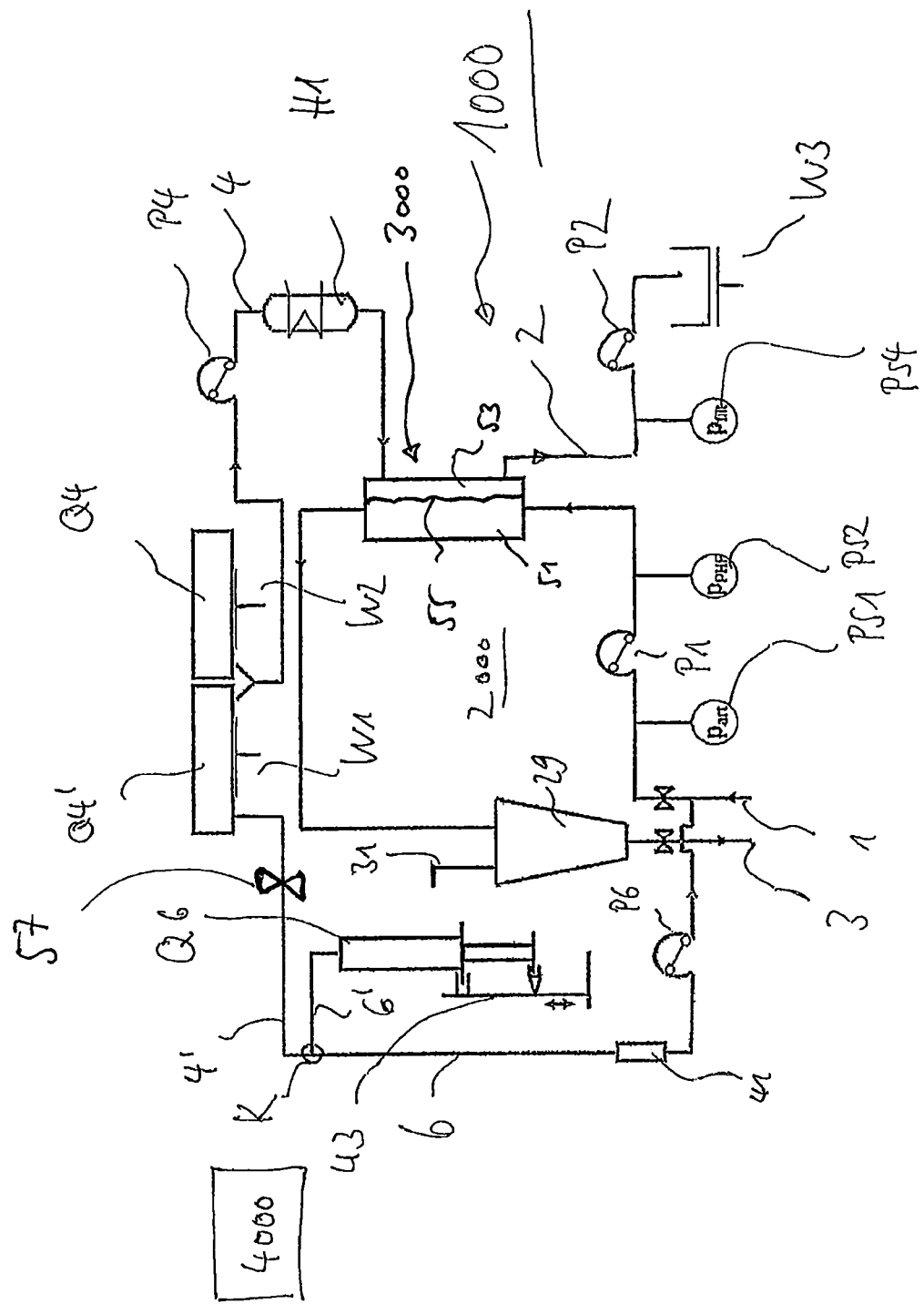

METHOD AND APPARATUSES FOR PREPARING AN EXTRACORPOREAL BLOOD CIRCUIT FOR THE TREATMENT OF BLOOD

CROSS-REFERENCE TO RELATED APPLICATIONS

This application is the national stage entry of International Patent Application No. PCT/EP2015/071677, filed on Sep. 22, 2015, which claims priority to German Patent Application No. 10 2014 113 728.0, filed on Sep. 23, 2014, the entire contents of which are hereby incorporated by reference.

TECHNICAL FIELD

The present disclosure concerns a method for preparing an extracorporeal blood circuit for the treatment of blood. In addition, it concerns a control unit as well as a blood treatment apparatus. Furthermore, the present disclosure concerns a digital storage medium, a computer program product as well as a computer program.

BACKGROUND

In practical extracorporeal blood treatment using an extracorporeal blood circuit, it is required and usual to prime the extracorporeal blood circuit before starting the blood treatment. This is understood to be a filling of the extracorporeal blood circuit, which after its establishment is filled with air, using a liquid fluid, which aims to prevent the introduction of air into the vascular system of the patient later on.

SUMMARY

Aspects of the present disclosure relate to methods and apparatuses for preparing (including priming) of the extracorporeal blood circuit. The solution used for priming is described herein as priming solution. A priming solution can be a mixture of solutions, which are used together for priming.

Furthermore, a blood treatment apparatus, using which the method can be carried out, as well as a control unit provisioned to carry out the method, a suitable digital storage medium, a suitable computer program product and a suitable computer program are to be provided.

SUMMARY

Certain advantages achievable by the methods, can also be achieved in an undiminished way, by the apparatuses described herein.

The method concerns the preparation of an extracorporeal blood circuit for its use in the blood treatment of a patient, for which a blood treatment apparatus is used. The method can comprise the provision of a suitable blood treatment apparatus.

The suitable blood treatment apparatus possesses at least one blood treatment device, such as a blood filter or a dialyzer. Preferably, the blood treatment apparatus possesses a blood chamber and a dialysate chamber separated therefrom by means of a membrane.

For the purpose of treating the blood of the patient the blood treatment apparatus possesses the following units and/or apparatuses or is connectable or connected with such in fluid and/or signal connection.

The method comprises a filling of the extracorporeal blood circuit or predetermined sections thereof using a priming solution. This occurs prior to the start of the blood treatment. The priming solution contains citrate. Alternatively, or in addition, the method comprises a filling of the extracorporeal blood circuit or predetermined sections thereof using a priming solution as well as a citrate solution, which is, for example, concentrated or highly concentrated. The mixture of priming solution, for example in the form of a dialysis solution or a substitute, and a citrate solution is described herein, in a simplified manner, as priming solution, as long as it is used for priming.

The control or regulating unit is suitable and intended and/or adapted and/or configured and/or programmed for carrying out at least one embodiment of the method, in particular in interaction with the required devices, for example as described herein.

In certain embodiments, the blood treatment apparatus possesses at least one control or regulating unit, which is preferably programmed to carry out the method in interaction with further devices, in particular of a blood treatment apparatus.

The blood treatment apparatus is intended and/or adapted and/or equipped for carrying out the method.

A digital, in particular non-volatile, storage medium, in particular in the form of a machine readable carrier, in particular in the shape of a floppy disk, CD, EPROM or DVD, with electrically readable control signals, can interact with a programmable computer system such that the machine steps of a method can be prompted.

In this, all or some of the steps of the method, executed by machine can be prompted.

A computer program product possesses a volatile program code or a program code stored in a machine readable carrier for prompting the machine steps of the method, if the computer program product is running on a computer. A computer program product can for example be a computer program stored on a carrier, an embedded system as a comprehensive system with a computer program (for example an electronic device with a computer program), a network of computer implemented computer programs (for example client/server system, cloud computing system etc.) or a computer onto which a computer program is loaded, run, stored, executed or developed.

The term "machine readable carrier", as used herein, denotes a carrier in certain embodiments, which contains data or items of information, which are interpretable by software and/or hardware. The carrier can be a data carrier, such as a floppy disk, a CD, a DVD, a USB stick, a flash card, an SD card or the like.

A computer program possesses a program code for the prompting of the machine steps of a method if the computer program is running on a computer. A computer program can be, for example, a physical, distributable software product, which contains a program.

For the computer program product and the computer program, all or some of the steps of the method are carried out by machine are prompted.

Certain embodiments can contain some or all of the following features in any combination as long as the combination is not technically impossible as recognized by the person skilled in the art.

In the following remarks, the use of the term "can be" or "can have" is synonymous to "is preferably" or "has preferably", respectively and is intended to illustrate certain embodiments.

Whenever numerals are used herein, the person skilled in the art will recognize these a lower limit. As long as this does not lead to a contradiction as recognized by the person skilled in the art, the skilled person will thus read "at least one" instead of "one". This interpretation is comprised by some embodiments as well as the interpretation that a numeral such as "one" will alternatively mean "exactly one", wherever this is technically possible as recognized by the person skilled in the art. Both are comprised by certain embodiments and are valid for all of the numerals used herein.

In some exemplary embodiments the priming solution is different from blood or is, optionally, free from blood altogether.

In certain exemplary embodiments, filling is carried out such that the priming solution, with which the extracorporeal blood circuit is filled, contains a maximum of 0.5 mmol/L or a maximum of 0.6 mmol/L of calcium, in particular in ionized form, in particular before the beginning of the blood treatment.

In some exemplary embodiments, the citrate solution, which is for example concentrated or highly concentrated, is added to the priming solution, before the extracorporeal blood circuit is filled with the priming solution.

In certain exemplary embodiments, the filling with a priming solution is carried out at pH 7.3, in particular measurable before the blood treatment.

In some exemplary embodiments, the priming solution possesses the usual physiologic composition, in particular before the beginning of the blood treatment.

In certain exemplary embodiments, the method further comprises the filling of the dialysate chamber of the blood treatment apparatus bypassing or across the membrane. In this, one part of the priming solution described herein (which, as is described above, may comprise citrate) propagates from the blood chamber of the blood cleaning apparatus, for example the blood filter, to the side of the dialysate chamber fills this more or less.

Alternatively, or additionally, the filling of the dialysate chamber can be through the fresh dialysis liquid side, with a solution, which possesses the same properties as the priming solution, at least concerning the calcium concentration and/or the citrate concentration.

In some exemplary embodiments, the method further comprises the establishment of a fluid connection between the arterial conduit section of the extracorporeal blood circuit and a source with citrate solution.

In some exemplary embodiments, the method further comprises the filling of the extracorporeal blood circuit or provisioned sections thereof using blood or a fluid, which contains or consists of blood. This filling still serves the preparation of the extracorporeal blood circuit and not the blood treatment of the patient. It can also take place after the priming described above. The extracorporeal circuit can be separated from the patient or can be separated anew after filling with blood. Its ends can, for example, be cut short.

In certain exemplary embodiments, the method further comprises the administration of a citrate solution to the blood, for example via a heparin pump. The administration can preferably be carried out in a section of the arterial conduit, which is arranged in close proximity to the patient connector or close to the location, at which blood is drawn from the patient. In this way, the blood is anticoagulated immediately after collection from the patient's vasculature.

In certain exemplary embodiments, the method further comprises the conveying of the fluid previously mentioned, for example blood, with which the extracorporeal circuit is now filled, within the extracorporeal circuit using a blood pump using a first conveying speed. It further comprises the simultaneous conveying of citrate from the source with citrate solution into the extracorporeal blood circuit using a second conveying apparatus using a second conveying speed. The second conveying speed has a set and/or predetermined ratio to the first conveying speed. Optionally the second conveying speed is later adjusted to this ratio, if necessary.

The first conveying speed can be, for example, 100 ml/min; the second conveying speed can be, when citrate is administered as a 4% trisodium citrate solution (136 mmol/L), 176 ml/h.

In some exemplary embodiments, the blood pump and the second conveying apparatus start together.

In certain exemplary embodiments, the dialysate flow is stopped or zero during the method.

In some exemplary embodiments, the previously mentioned fluid, with which the extracorporeal blood circuit is now filled, is conveyed within the extracorporeal blood circuit for at least until the fluid is present in all sections of the extracorporeal blood circuit or until it completely fills the extracorporeal blood circuit.

In some exemplary embodiments, the previously mentioned fluid, with which the extracorporeal blood circuit is now filled, is conveyed within the extracorporeal blood circuit, preferably using the blood pump, at least for a certain time period, until one layer of proteins is deposited in one or several surfaces of the extracorporeal blood circuit.

In certain exemplary embodiments, the previously mentioned fluid, with which the extracorporeal blood circuit is now filled, is conveyed within the extracorporeal blood circuit, for example using a blood pump, for at most a period of time, which does not make a calcium infusion, in order to avoid hypocalcemia. In certain embodiments, this period of time is, between 10 and 15 minutes, preferably between 12 and 13 minutes, more preferably 12.5 minutes.

In some exemplary embodiments, the fluid, with which the extracorporeal blood circuit is filled, is conveyed for a maximum time of 15 minutes and/or a minimum time of 3 minutes, preferably at least until the extracorporeal blood circuit is filled completely.

In some exemplary embodiments, the determination of a maximum amount of citrate, which is used/added, comprises at least the consideration of individual patient data, in particular his or her extracellular body water. Such data can be determined or estimated using BCM (body composition monitor). Suitable to this end is, for example, a bioimpedance measuring device, such as one produced by the applicant or by Xitron Technologies, marketed under the trade mark Hydra™, as described in WO 92/19153, the relevant portions of which are hereby included in the present disclosure by way of reference.

In some exemplary embodiments, the amount of citrate, which is added to the priming solution and/or the blood at the start or until the start of the blood treatment, is at most 5 mmol. This value can correspond to a worst case.

The typical citrate distribution volume is 25 to 30% of body weight. In a smaller patient with a body weight of 30 kg the distribution volume is thus 7.5 litres. The increase in citrate concentration in the blood through the infused 5 mmol of citrate is then 0.67 mmol/l, which is acceptable.

In certain exemplary embodiments, the control or regulation unit is programmed to carry out a blood treatment or to control or regulate the blood treatment apparatus after priming according to one of the embodiments described above, in interaction with a blood treatment apparatus, for example as described herein. In this, no heparin or other anticoagulant and/or no calcium, for example in the form of a calcium solution administered to influence coagulation, for example in a concentration of more than 5 mmol/L, is added to the extracorporeal blood circuit and/or the patient during the blood treatment.

In some exemplary embodiments, in the blood treatment method following the priming, the blood pump is set initially to be slower than later and later to be faster than earlier.

A citrate solution in some embodiments contains citrate as described in US 2006/0037910 A1 and in particular in the paragraphs [0040] to [0042] therein. The relevant portions of which are hereby included in the subject matter of the present application by way of reference.

In certain exemplary embodiments, the blood treatment apparatus is a hemodialysis apparatus, hemofiltration apparatus or hemodiafiltration apparatus.

The extracorporeal blood circuit is in certain embodiments a tube set. In any case, the extracorporeal blood circuit is intended for the extracorporeal guiding of blood of a patient, for example during hemodialysis, hemofiltration, hemodiafiltration or the like.

In some embodiments, the extracorporeal blood circuit is at least in sections designed as an integral and, if applicable, inseparable part of a blood cassette, in others, it is not. In this way a freely movable tube section of the extracorporeal blood circuit can continue integrally on or in the operating unit, for example a blood cassette, and vice versa.

A blood cassette in certain embodiments is a unit, which is used in blood treatment. Examples for blood cassettes include disposables, single use blood cassettes.

Exemplary embodiments of a blood cassette are disclosed in particular in the application of the applicant with the publication number DE 10 2009 018 664 A1 titled "Externe Funktionseinrichtung, Blutbehandlungsvorrichtung zum Aufnehmen einer erfindungsgemäßen externen Funktionseinrichtung, sowie Verfahren", which was filed at the German Patent and Trademark Office on 23 Apr. 2009 as well as in the application of the applicant with the publication number DE 10 2009 024 468 A1 by the same title, which was filed on 10 Jun. 2009 at the German Patent and Trademark Office. The disclosures of these two applications are incorporated by reference in their entirety.

The arterial conduit section of the extracorporeal blood circuit is, in certain embodiments, the section, into which the patient's blood flows leaving the patient's body with the purpose of extracorporeal blood treatment and in which it is located before entering into the blood treatment apparatus, for example a dialyzer.

In certain embodiments, the first section of the arterial conduit section is or comprises the arterial needle connector to the patient, for example the arterial needle connector in a double needle dialysis method.

The venous conduit of the extracorporeal blood circuit is, in some embodiments, the section, from which the extracorporeally treated blood of the patient flows towards the patient's body or back from it, after its treatment in a blood treatment device, for example a dialyzer.

In certain embodiments, the first conveying direction, which is typical during blood treatment, corresponds to a conveying direction from the arterial line (place of blood withdrawal) of the patient to a blood treatment device, for example a blood filter or a dialyzer, and subsequently through the venous conduit of the extracorporeal circuit to the venous line (place of blood return) of the patient. All devices, which are located in the first conveying direction relative to a reference point of the flow path, are located downstream thereof. Such units, which are located against the first conveying direction, relative to a reference point, are located upstream thereof.

The control unit is implemented as a regulating unit in some embodiments.

Some or all of the embodiments can possess one, several or all of the advantages mentioned above or in the following.

One advantage that can be achieved by some embodiments of the methods and apparatuses described herein is that the extracorporeal blood circuit can be prepared for a blood treatment in such a way that the blood treatment can be carried out without the use of heparin. In view of the fact that there are dialysis patients, for example, who suffer from an intolerance to heparin, this offers significant advantages. Furthermore, it protects such patients that are not aware that they have an intolerance to heparin.

The method may be a contribution to the reduction of complications in heparin free dialysis. It may be indicated in particular in patients, who suffer from heparin induced thrombocytopenia (HIT), or in postoperative patients.

In addition to the aspect of patient protection in the case of such heparin intolerance, certain methods and apparatuses described herein offer the further advantage that heparin, as an expensive substance, can be economized, which is beneficial to all patients, even those who do not possess an intolerance of heparin.

Furthermore, it can be advantageous that in some embodiments, the addition of citrate during the entire blood treatment course is not necessary. Such a continuous citrate treatment would, as is well-known, absolutely require that the physiologic calcium concentration of the treated blood is restored by infusing the blood with a calcium containing substitutional solution. To this end, the required calcium concentration must be determined. This is complex and involves additional laboratory controls of the patient's blood.

By limiting the anticoagulation, entirely or essentially, to a small citrate volume at first contact with the blood, complex regulation of the calcium reinfusion can be eliminated.

In this, the variation of the bicarbonate concentration, common in dialysis, suffices to control the acid-base balance. Thus, in clinical routine and without staff specifically trained and experienced in citrate anticoagulation, further risks are reduced, such as, for example, hypo- or hypercalcemia, or large shifts in the acid-base balance.

By preventing patient complications induced by heparin, as carried out above, the required effort and use of personnel to remedy such complications can be avoided. The loss of blood occurring regularly during such complications on account of coagulation, which blood may have to be restored to the patient by applying blood transfusions, can be prevented by avoiding complications.

BRIEF DESCRIPTION OF THE FIGURE

In the following, the present invention is described using the enclosed FIGURE, purely exemplarily.

FIG. 1 shows a simplified representation of an exemplary embodiment of a blood treatment apparatus with an extracorporeal blood circuit.

DETAILED DESCRIPTION OF THE FIGURE

FIG. 1 shows in a simplified representation a blood treatment apparatus 1000 with an extracorporeal blood circuit 2000.

The extracorporeal blood circuit 2000 possesses a blood treatment device 3000, here exemplarily a blood filter or dialyzer with a blood chamber 51, a dialysate chamber 53 and a membrane 55 or is connected to the blood treatment unit 3000. An arterial conduit section 1 of the extracorporeal blood circuit 2000 guides blood from the vascular system of the patient (not shown) in direction of the blood filter 3000. A venous conduit section 3 of the extracorporeal blood circuit 2000 guides blood from the blood filter 3000 in the direction of the vascular system of the patient (not shown).

The blood treatment apparatus 1000, which is represented only by some of its devices in FIG. 1, possesses a blood pump; the method described herein is carried out using said blood treatment apparatus. The blood pump P1 conveys blood through sections of the extracorporeal blood circuit 2000 and towards the blood filter 3000, as shown by the small arrowheads, which in the FIGURE show the direction of flow in general.

In addition to the previously mentioned pump P1, the arrangement in FIG. 1 possesses a purely optional series of further pumps P2, P4 and P6.

The pump P4 is one of the optional pumps. It is intended to guide dialysis fluid using a dialysis fluid conduit 4 from a source Q4, for example a bag, to the dialysate chamber 53 via an optionally present bag heater with bag H1.

The dialysis liquid thus supplied exits via a dialysate conduit 2, optionally supported by a pump P2, and can be discarded.

The optional pump P6 pumps a combined fluid of priming solution and citrate solution, for reasons of simplicity referred to as priming solution in the following, along a conduit 6, here to be understood as a common conduit, into the arterial conduit 1. Instead of by the pump P6, this function can be carried out solely by the blood pump P1 as well. The pump P6 can therefore be dispensed with.

The priming solution originates, for example, from a first source Q4', here exemplarily a bag with dialysis fluid (it could also be substitute, NaCl solution or another solution or liquid), and is first conveyed to the intersection point K in the first conduit 4'.

The citrate solution originates from a second source Q6, here a syringe with citrate or a citrate concentrate ("Ci-concentrate"), and is first conveyed to the intersection point K in a second conduit 6'. The syringe contains its own conveying device, here a syringe pump, which is not shown. It is clear to see for the person skilled in the art that such a syringe pump is at least not necessary when the second source Q6 is not a syringe but for example a bag. In this case, the conveying device is a pump and is not optional.

From the intersection point or connecting point K, the first conduit 4' and the second conduit 6' become or flow into the common conduit 6.

In the present example, the first source Q4' and the source Q4 are sources independent of each other for the same fluid, i.e., dialysis fluid. The invention comprises also, however, that Q4 and Q4' are one and the same source or are in fluid communication with each other.

Upstream of the blood pump P1, an optional arterial sensor PS1 is provisioned, which measures the arterial pressure P_art.

Downstream of the blood pump P1, but upstream of the blood filter 3000, a further, optional pressure sensor PS2 is provisioned. It measures the pressure upstream of the blood filter 3000 (PHF stands for "pre-hemofilter").

A further pressure sensor can be provisioned as PS4 downstream of the blood filter 3000, but upstream of the pump P2 in the dialysate conduit 2 for measuring a filter pressure of the blood filter 3000.

Blood, which leaves the blood filter 3000, streams through the venous blood chamber 29, which can possess a de-aeration device 31.

In the example of FIG. 1, the sources Q4 and Q4' and the collected or discarded spent dialysate are optionally subject to a balancing. Three scales W1, W2 and W3 are provided for the purpose of the optional balancing.

The examples shown here correspond to a gravimetric balancing. The present invention encompasses, however, is not restricted to this balancing mechanism.

The exemplary arrangement shown in FIG. 1 possesses optionally a first monitoring device 41. It is designed for the monitoring of the correct function and/or for the determining of a feed rate or a feed volume of the pump P6.

The exemplary arrangement shown in FIG. 1 further optionally comprises a second monitoring device 43. It is designed for monitoring the correct function and/or for detecting a feed rate or a feed volume of the second conveying device, in this case of the syringe pump, of the second source Q6. The second monitoring device 43 is purely optional and is recognizably designed as a distance sensor. Both the first and the second monitoring device 41, 43 may be designed as drop counters. Both the first and the second monitoring device 41, 43 may be connected to a comparing device, which is not shown in the figures.

A controlling or regulating unit 4000 is indicated in FIG. 1. It is in signal connection with all the relevant devices, in any case with the blood pump P1 and preferably also with the pump P6 or the syringe pump.

The following features can, though not shown in the figures, be provisioned in any embodiment, purely optionally and in any combination:

The arterial conduit section 1 can comprise an arterial clamp.

The arterial conduit section 1 can comprise an arterial septum, optionally in the shape of an addition device.

The venous conduit section 3 may comprise a venous air bubble detector/optical sensor.

The venous conduit section 3 can comprise a venous clamp.

The arterial conduit section 1 may comprise an arterial air bubble detector/optical sensor.

In the following, a possible embodiment, which can be implemented using the arrangement of FIG. 1, is described, in which the interaction between blood and extracorporeal blood circuit during the initial phase is substantially reduced.

To this end, the priming solution as well as the initial blood volume is anticoagulated with citrate in such a way that the coagulation is effectively inhibited. On the other hand, the total amount of infused citrate is chosen such that an infusion of calcium for avoiding an acute hypocalcemia is not required and no undesired shift of the acid-base balance results.

When priming using priming solution, citrate is used in a first step in order to prevent the diffusion of calcium from the dialysate into the blood compartment in the initial blood treatment phase, which follows priming and which is carried out at a relatively low blood flow. The citrate concentration to be used is thus dependent on the calcium concentration in the priming solution. The resulting calcium concentration in the priming solution is preferably below 0.5 mmol/L.

In a second step, citrate anticoagulated blood is pumped into the extracorporeal circuit over a limited period of time at a blood flow, which is preferably low, for example 100 ml/min. In this way, a coating of the blood filter 3000 with endogenous proteins is meant to be achieved. The citrate concentration in the blood to be achieved in this phase can preferably be 4 mmol/l. As a citrate solution, for example, a 4% trisodium citrate solution (136 mmol/l) can be used. At a blood flow of 100 ml/min this would mean a citrate flow of 176 ml/h.

The blood should be anticoagulated for at least as long until the extracorporeal blood circuit is filled once, i.e., until blood alarm has been triggered, i.e., until blood in the blood circuit has been detected by a sensor in the blood circuit, possibly for a few minutes longer.

When the incubation of the extracorporeal circuit with citrate anticoagulated blood is completed, the remaining part of the treatment is carried out without anticoagulant or with a reduced amount of anticoagulant and with a higher blood flow. A single bolus administration of heparin to the patient before treatment start is possible. All in all, a reduction of the amount of heparin is achieved.

The method can roughly be divided into two separate, consecutive phases, phase 1 and phase 2. In phase 1, the extracorporeal circuit is filled with priming solution. When this is accomplished, it is filled with a solution, which—through the addition of citrate—contains <0.5 mmol/L ionized calcium and preferably has a pH above 7.3 (in order to avoid contact phase activation) and which possesses the physiologic composition, which is common otherwise.

Furthermore, it is advantageous that the contents of the dialysate chamber 53 of the blood filter 3000 have the same solution composition as the remaining blood circuit 2000. This is to prevent that the calcium of the dialysis fluid diffuses into the blood circuit 3000 and thus increases the concentration of the ionized calcium.

In phase 2, the extracorporeal blood circuit 2000 is filled with blood. A concentrated citrate solution is fed to the arterial section of the of the extracorporeal blood circuit 2000 using a dosing unit (for example the heparin pump). Ideally, this takes place close to the connector of the arterial needle in order to anticoagulate the blood preferably immediately after the removal from the body.

After the arterial needle is connected to the arterial conduit section 1, for example the following filling routine is started automatically or manually: The blood pump P1 and the citrate infusion pump start at the same time. The pump P6 can be understood to be the citrate infusion pump, at a closed clamp 57. In this, the blood pump controls the speed of the citrate infusion pump via an adjustable transmission ratio. Thereby, it is achieved that the ionized calcium concentration in the blood is adjusted to the intended low level for complete anticoagulation. The speed of the blood pump P1 in turn is determined by ensuring that the (adjustable) time, in which the blood flows across the areas or surfaces of the extracorporeal blood circuit 2000, is sufficiently long to build up a secondary protein layer thereon, and that the adjustable time is sufficiently short to not require a calcium infusion for the avoidance of a hypocalcemia in the patient and to avoid a relevant hypernatremia or alkalosis.

The inflow of dialysis fluid is stopped during this process.

The amount of citrate, which can safely be administered to a patient should be determined using parameters characterizing the patient (automatically or via manual input). To this end, ideally, information on the volume of his or her extracellular body water is to be used, for example from BCM data. In the literature there are references on the amount of citrate that can be administered.

For the calculation of the time for the infusion one or several of the following factors is to be considered:

the extracorporeal blood volume
the decision, whether start up is carried out synchronously (i.e., artery and vein at the same time) or using bloodletting (i.e., the priming solution is discarded until blood is detected in the venous line system)
the minimal blood pump speed
the minimal time to conclude the initial protein absorption

REFERENCE NUMERAL LIST 1000 blood treatment apparatus
2000 extracorporeal blood circuit
3000 blood treatment device, blood filter or dialyzer
4000 control or regulating unit
1 arterial conduit section
2 spent dialysate conduit
3 venous conduit section
4 fresh dialysate conduit
4' first conduit coming from first source
5 joint or common conduit
6' second conduit coming from second source
H1 bag heater with bag
P1 blood pump
P2, P4, P6 optional pumps
PS1 arterial sensor, measures the arterial pressure P_art
PS2 optional pressure sensor
PS4 pressure sensor for measuring a filter pressure
Q4 source with fresh dialysate
Q4' first source
Q6 second source
29 venous blood chamber
31 de-aeration device
K crossing point or intersection point or connection point of the first conduit with the second conduit
W1, W2, W3 scales
41 first monitoring device
43 second monitoring device
51 blood chamber
53 dialysate chamber
55 membrane
57 closed clamp

The invention claimed is:

1. A method of preparing an extracorporeal blood circuit for use in a blood treatment of a patient, which treatment is carried out using a blood treatment apparatus and using a blood treatment device, which comprises a blood chamber and a dialysate chamber partitioned off therefrom by a membrane, the method comprising:
    filling the extracorporeal blood circuit with a first priming solution, wherein the first priming solution comprises citrate, or filling the extracorporeal blood circuit with a second priming solution and a citrate solution; and
    filling the extracorporeal blood circuit with a fluid comprising or consisting of blood while no dialysis fluid flows through the dialysate chamber of the blood treatment device.

2. The method according to claim 1, wherein the first priming solution or the second priming solution and the citrate solution, with which the extracorporeal blood circuit is filled, comprises a maximum of 0.5 mmol/L calcium.

3. The method according to claim 1, wherein the first priming solution or the second priming solution and the citrate solution, with which the extracorporeal blood circuit is filled, possesses a pH of at least 7.3.

4. The method according to claim 1, comprising:
establishing a fluid connection between an arterial conduit section of the extracorporeal blood circuit and a source of citrate solution.

5. The method according to claim 1, comprising:
conveying the fluid within the extracorporeal blood circuit using a blood pump at a first conveying speed; and
simultaneously conveying citrate from a source of citrate solution into the extracorporeal blood circuit using a second conveying apparatus at a second conveying speed;
wherein the second conveying speed is in an adjusted or predetermined ratio to the first conveying speed.

6. The method according to claim 5, wherein the fluid is conveyed within the extracorporeal blood circuit using the blood pump at least for a certain time period until a layer of protein is deposited on one or several surfaces of the extracorporeal blood circuit.

7. The method according to claim 5, wherein the fluid is conveyed within the extracorporeal blood circuit using the blood pump at most for a time period, which does not necessitate a calcium infusion for the avoidance of a hypocalcemia.

8. The method according to claim 7, where in the time period is between 10 and 15 minutes.

9. The method according to claim 5, further comprising readjusting the ratio of the second conveying speed to the first conveying speed.

10. The method according to claim 1, comprising:
determining a maximum amount of citrate, which is used or administered, considering individual data of the patient, the individual data comprising a measurement of extracellular body water volume of the patient.

11. A control or regulating unit suitable and provisioned, designed, configured, or programmed for carrying out a method comprising:
preparing an extracorporeal blood circuit for use in a blood treatment of a patient, which treatment is carried out using a blood treatment apparatus and using a blood treatment device, which comprises a blood chamber and a dialysate chamber partitioned off therefrom by a membrane;
filling the extracorporeal blood circuit with a first priming solution, wherein the first priming solution comprises citrate, or filling the extracorporeal blood circuit with a second priming solution and a citrate solution; and
filling the extracorporeal blood circuit with a fluid comprising or consisting of blood while no dialysis fluid flows through the dialysate chamber of the blood treatment device.

12. The control or regulating unit according to claim 11, additionally programmed to carry out a blood treatment together with the blood treatment apparatus, wherein during the blood treatment, at least one of heparin and calcium is not added to the blood guided in the extracorporeal blood circuit.

13. A blood treatment apparatus, comprising a control or regulating unit, which is programmed to carry out a method comprising:
preparing an extracorporeal blood circuit for use in a blood treatment of a patient, which treatment is carried out using a blood treatment apparatus and using a blood treatment device, which comprises a blood chamber and a dialysate chamber partitioned off therefrom by a membrane;
filling the extracorporeal blood circuit with a first priming solution, wherein the first priming solution comprises citrate, or filling the extracorporeal blood circuit with a second priming solution and a citrate solution; and
filling the extracorporeal blood circuit with a fluid comprising or consisting of blood while no dialysis fluid flows through the dialysate chamber of the blood treatment device.

14. The blood treatment apparatus according to claim 13, wherein the blood treatment apparatus is a hemodialysis device, a hemofiltration device or a hemodiafiltration device.

15. A digital storage medium, in particular in the form of a disk, with electrically readable control signals, configured for interacting with a programmable computer system such that the mechanical steps of the method according to claim 1 is prompted.

16. A computer program product with a program code saved on a machine-readable medium for prompting the mechanical steps of the method according to claim 1, when the computer program product runs on a computer.

* * * * *

UNITED STATES PATENT AND TRADEMARK OFFICE
CERTIFICATE OF CORRECTION

PATENT NO. : 10,646,635 B2  
APPLICATION NO. : 15/513187  
DATED : May 12, 2020  
INVENTOR(S) : Robert Pohlmeier and Wofgang Wehmeyer Page 1 of 1

It is certified that error appears in the above-identified patent and that said Letters Patent is hereby corrected as shown below:

On the Title Page

Column 1, (72) Inventors, Line 2, delete "Wofgang Wehmeyer" and insert --Wolfgang Wehmeyer--.

Column 2, (57) Abstract, Line 6, delete "membrane," and insert --membrane.--.

In the Specification

Column 10, Line 20, delete "5 joint of common conduit" and insert --6 joint or common conduit--.

In the Claims

Claim 15, Column 12, Line 34, after "medium," delete "in particular".

Signed and Sealed this  
Twentieth Day of July, 2021

Drew Hirshfeld  
*Performing the Functions and Duties of the*  
*Under Secretary of Commerce for Intellectual Property and*  
*Director of the United States Patent and Trademark Office*